United States Patent
De Knaep et al.

(10) Patent No.: US 6,218,542 B1
(45) Date of Patent: Apr. 17, 2001

(54) SYNTHESIS OF CISAPRIDE

(75) Inventors: Alfons Gaston Maria De Knaep, Turnhout; Luc Jozef Raphael Moens, Lille, both of (BE); Max Rey, Zurich (CH)

(73) Assignee: Jenssen Pharmaceutica N.V. (BE)

( * ) Notice: Subject to any disclaimer, the term of this patent is extended or adjusted under 35 U.S.C. 154(b) by 0 days.

(21) Appl. No.: 09/284,513

(22) PCT Filed: Oct. 9, 1997

(86) PCT No.: PCT/EP97/05692

§ 371 Date: Apr. 14, 1999

§ 102(e) Date: Apr. 14, 1999

(87) PCT Pub. No.: WO98/16511

PCT Pub. Date: Apr. 23, 1998

(30) Foreign Application Priority Data

Oct. 15, 1996 (EP) .................................................. 96202860

(51) Int. Cl.⁷ .................................................. C07D 211/58
(52) U.S. Cl. ........................ 546/216; 546/221; 546/224; 514/326; 514/327; 514/329
(58) Field of Search ..................... 514/326, 327, 514/329; 546/216, 221, 224

(56) References Cited

U.S. PATENT DOCUMENTS

| | | | |
|---|---|---|---|
| 4,962,115 | * 10/1990 | Van Daele | 514/326 |
| 5,047,581 | * 9/1991 | Palmers et al. | 562/506 |
| 5,057,525 | * 10/1991 | Van Daele | 514/318 |
| 5,137,896 | * 8/1992 | Van Daele | 514/327 |
| 5,618,828 | * 4/1997 | Gray et al. | 514/327 |
| 5,629,329 | * 5/1997 | Gray et al. | 514/327 |
| 5,712,293 | * 1/1998 | McCullough et al. | 514/327 |
| 5,739,151 | * 4/1998 | McCullough et al. | 514/327 |

FOREIGN PATENT DOCUMENTS

| | | |
|---|---|---|
| 0 074 792 | * 3/1983 | (EP) . |
| 0 052 510 | 10/1994 | (EP) . |
| 2 002 640 | * 1/1988 | (ES) . |

OTHER PUBLICATIONS

Cisapride CAS–RN 81098–60–4.*
Morrison and Boyd "Organic chemistry" p. 306–307, 1973.*
Van Daele G. H. P. et al: "Synthesis Of Cisapride, A Gastrointestinal Stimulant Derived From Cis–4–Amino–3–Methoxypeperidine" Drug Development Research, vol. 8, Jan. 1, 1986, pp. 225–232.*
Abstract of ES 2002640, (1988).*

* cited by examiner

Primary Examiner—Ceila Chang

(57) ABSTRACT

A new Process of preparing cisapride, and the pharmaceutically acceptable acid addition salts thereof, by reductively aminating 1-[3-(4-fluorophenoxy)-propyl]-3-methoxy-4-piperidinone in the presence of benzylamine under hydrogen in a reaction-inert solvent, yielding 1-[3-(4-fluorophenoxy)-propyl]-3-methoxy-4-piperidinamine having a cis/trans ratio of about 93/7, which is enriched in the amount of cis-stereoisomer by converting it into its acid addition salt, by treatment with a suitable inorganic acid, in an appropriate solvent, subsequent crystallisation and conversion to its free base form by treatment with an appropriate base, yielding 1-[3-(4-fluorophenoxy)-propyl]-3-methoxy-4-piperidinamine having a cis/trans ratio of equal to or higher than 98/2.

9 Claims, No Drawings

SYNTHESIS OF CISAPRIDE

This application is a 371 of PCT/EP97/05692 filed Oct. 9, 1997.

The present invention is concerned with a new process of preparing cisapride having the formula

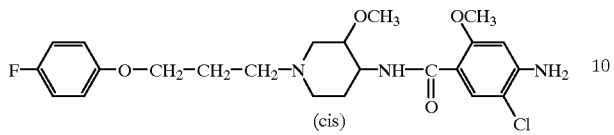

and is pharmaceutically acceptable acid addition salts thereof.

European Patent No. 0,076,530 discloses the gastroprokinetic agent cisapride, classic compositions thereof and processes for its preparation. The systematic chemical name of cisapride is cis-4-amino-5-chloro-N-[1-[3-(4-fluorophenoxy)-propyl]-3-methoxy-4-piperidinyl]-2-methoxybenzamide. Cisapride is a racemic mixture of two enantiomers. Cisapride has excellent gastrointestinal motility stimulating properties and is reported to be devoid of antidopaminergic activity. Its utility in a variety of gastrointestinal disorders has already been reported extensively.

Cisapride has a cis-stereochemistry between the substituents on the 3 and 4 position of the piperidinyl moiety. The desired cis-stereochemistry is preferably introduced by synthesizing intermediates having said cis-stereochemistry in order to a void the—sometimes difficult—separation of the cis- and trans-stereoisomer of cisapride or their precursors, in the later stages of the preparation process.

Processes of preparing cisapride have been described in Spanish patents ES-0,537,948 and ES-2,019,011. In ES-2,020,128 and ES-2,019,234, cisapride is prepared by hydrogenation of its pyridinium iodide analogue, and ES-2,019,235 describes the preparation of cisapride by hydrogenation of its tetrahydropyridine analog.

In ES-0,550,123 and ES-2,002,640, cisapride is prepared by reacting 4-amino-5-chloro-2-methoxybenzoic acid with cis-4-amino-1-[3-(4-fluorophenoxy)-propyl]-3-methoxy-4-piperidine or a derivative thereof.

Cisapride can also be prepared starting from cis-4-amino-3-methoxy-1-piperidine-carboxylic acid ethyl ester, as described in Van Daele G. et al., *Drug Dev. Res.*, 8(1-4), 225–232 (1986), ES-2,019,047 and EP-0,076,530.

In WO-96/11186, cisapride is prepared by reducing a 3-oxo-4-arylamido-piperidine derivative in the presence of potassium selectride thereby introducing a hydroxy group on the 3 position of the piperidine moiety having a cis-orientation with respect to the substituent on the 4-position, followed by deprotecting the amino group and methylating the hydroxy group on the piperidine moiety.

Another art process for preparing the tritiated analogue of cisapride, as depicted herebelow in scheme 1, is described by Janssen C. G. M. et al. in *J. Labelled Comp. Radiopharm.*, 24:1493–1501 (1987).

Scheme 1

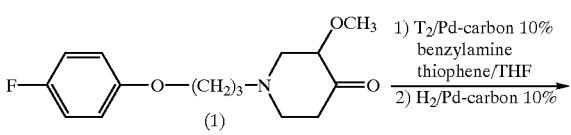

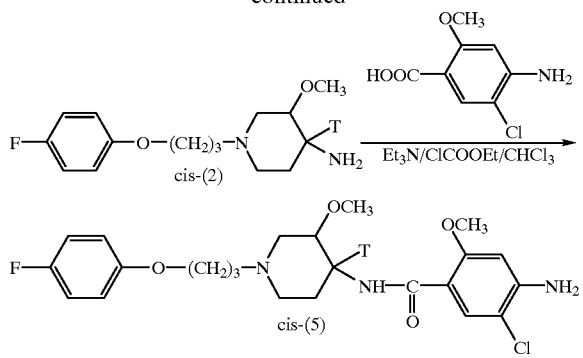

In scheme 1, tritiated cisapride (5) was obtained by reductive amination of 1-[3-(4-fluorophenoxy)propyl]-3-methoxy-4-piperidinone (1) with benzylamine under tritium, followed by catalytic debenzylation and subsequent amidation with the mixed anhydride of 4-amino-5-chloro-2-methoxy-benzoic acid (3) and ethyl chloroformate. On an industrial scale, cisapride is prepared via a completely analogous route.

A problem encountered in the industrial process is the formation of small amounts of intermediates having a trans stereochemistry. Since said trans-intermediates yield the trans-stereoisomer of cisapride, which is not easily separated from the desired cis-stereoisomer, there is a need for a process yielding intermediates having a more favourable cis/trans ratio. Such a process is economically advantageous.

We have found that certain intermediates of cisapride can be enriched in the amount of cis-stereoisomer by their conversion to a salt form and subsequent selective crystallisation.

Hence, the present invention relates to a process of enriching the amount of cis-stereoisomer in compounds of formula (I) by converting said compounds (I) to acid addition salts of formula (I-a) and subsequent crystallisation. The acid addition salts of formula (I-a) can optionally be converted by treatment with an appropriate base to their free base form of formula (I) thereby yielding said compounds of formula (I) enriched in the amount of cis-stereoisomer.

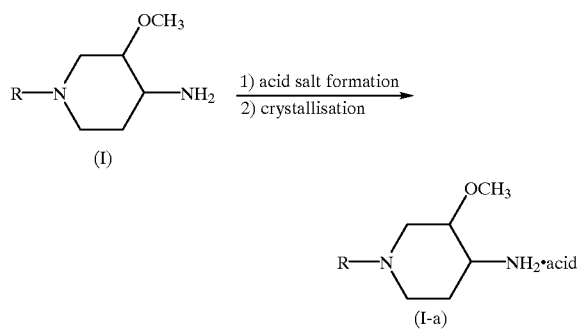

In compounds of formula (I) and (I-a) the substituent R represents hydrogen, $C_{1-6}$alkyl, $C_{1-6}$alkylcarbonyl, $C_{1-6}$alkyloxycarbonyl, phenylmethyl or 4-fluorophenoxypropyl.

Said process encompasses the conversion of compound (I) to an acid addition salt by treating compound (I) with a suitable acid, in an appropriate solvent such as, e.g. dichloromethane, chloroform, methanol, ethanol, isopropanol, n-butanol, acetone, 4-methyl-2-pentanone (MIK), toluene and the like, or mixtures thereof. Subsequent crystallisation yields compound (I-a) wherein the amount of cis-stereoisomer is enriched. Suitable acids are inorganic acids such as, for example, hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

In particular, the present invention relates to a process of enriching the amount of cis-stereoisomer of a compound of formula (I-1).

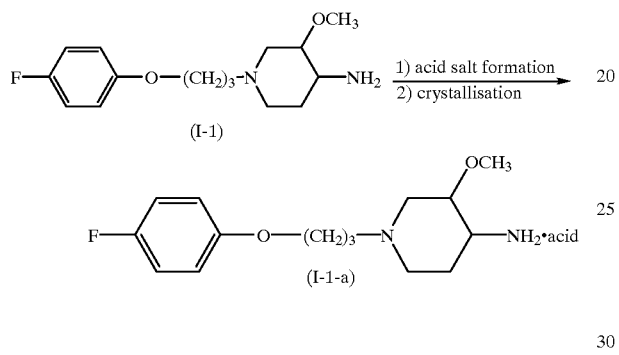

This can be accomplished by converting compound (I-1) to an acid addition salt by treating compound (I-1) with a suitable inorganic acid such as, e.g. hydrochloric or nitric acid and the like, in an appropriate solvent such as, e.g. isopropanol, n-butanol, 4-methyl-2-pentanone (MIK), toluene and the like. Subsequent crystallisation yields compound (I-1-a) wherein the amount of cis-stereoisomer is enriched to be equal to or higher than 98%. Conversely said acid addition salt form, compound (I-1-a), can be converted by treatment with an appropriate base to its free base form. Table 1 lists an overview of various acid addition salt formation experiments, each yielding compound (I-1) with a cis/trans ratio equal to or higher than 98/2. The column "mol/mol" lists the ratio acid/compound (I-1) used in the experiments. The yields of isolated product mentioned in table 1 are indicative and may be improved by changing the conditions, e.g. temperature, crystaflisation time, seeding frequency and concentration. during crystallisation of compound (I-1-a).

TABLE 1

| cis/trans* | solvent | acid | mol/mol | yield | cis/trans** |
|---|---|---|---|---|---|
| 92.5/7.1 | isopropanol | HCl | 1/1 | 69.0 | 98.9/0.9 |
| 93.0/7.0 | isopropanol | HCl | 1.05/1 | 69.1 | 99.25/0.75 |
| 92.0/8.0 | n-butanol | HNO$_3$ (65%) | 1.3/1 | 32.7 | 100.0/0.0 |
| 93.0/7.0 | MIK | HNO$_3$ (65%) | 1/1 | 86 | 99.2/0.8 |
| 92.0/8.0 | toluene | HNO$_3$ (65%) | 0.65/1 | 68.4 | 98.4/1.6 |

*cis/trans ratio before purification of compound (I-1)
**cis/trans ratio of compound (I-1-a)

The present invention also concerns a process of preparing cisapride and the pharmaceutically acceptable acid addition salts thereof as depicted in scheme 2.

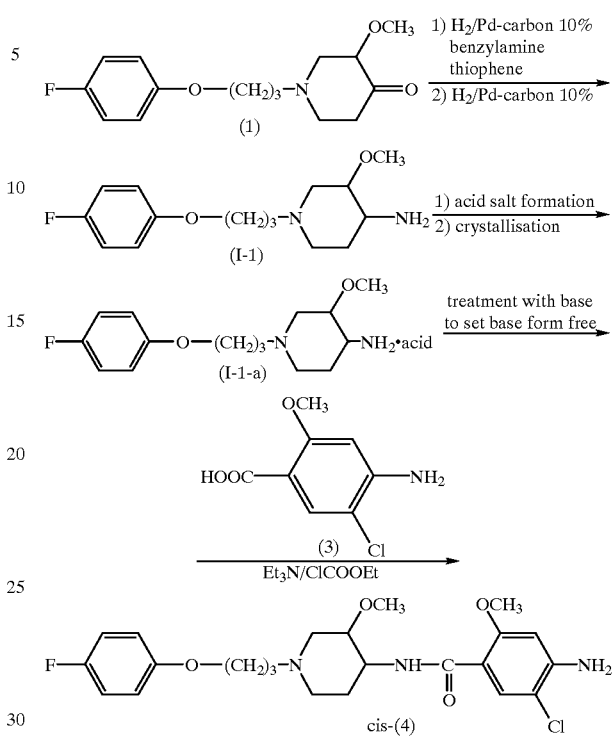

In scheme 2, 1-[3-(4-fluorophenoxy)propyl]-3-methoxy-4-piperidinone (1) is reductively aminated with benzylamine under hydrogen, in a reaction-inert solvent such as, an alcohol, e.g. methanol, an ether, e.g. tetrahydrofuran, or an aromatic hydrocarbon, e.g. toluene, and the like; yielding compound (I-1). Subsequent conversion of compound (I-1) to an acid addition salt yields, after crystallisation, compound (I-1-a) wherein the amount of cis-stereoisomer is enriched to be equal to or higher than 98%. Compound (I-1-a) is treated with a base to set the cis-stereoisomer enriched compound (I-1) free and subsequently treated with the mixed anhydride of 4-amino-5-chloro-2-methoxybenzoic acid (3) and ethyl chloroformate in a reaction-inert solvent such as, a halogenated hydrocarbon, e.g. chloroform; an ether, e.g. tert-butyl methyl ether or tetrahydrofuran; a ketone, e.g. 4-methyl-2-pentanone; or an aromatic hydrocarbon, e.g. toluene; and the like; yielding cisapride (4).

Also, cisapride (4) may be synthesized by treating an acid addition salt of formula (I-1-a) with the mixed anhydride of 4-amino-5-chloro-2-methoxybenzoic acid (3) and ethyl chloroform ate.

The pharmaceutically acceptable addition salts of cisapride as mentioned hereinabove are meant to comprise the therapeutically active non-toxic acid addition salt forms which cisapride is able to form. Cisapride can be converted in its pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

As used in the foregoing definitions $C_{1-6}$alkyl defines straight and branched chain saturated hydrocarbon radicals having from 1 to 6 carbon atoms such as, for example, methyl, ethyl, propyl, butyl, 1-methylethyl, 2-methylpropyl, 2-methylbutyl, pentyl, hexyl and the like.

The term addition salts also comprises the hydrates and the solvent addition forms which cisapride is able to form. Examples of such forms are e.g. hydrates, alcoholates and the like.

EXPERIMENTAL PART

Hereinafter, "MIK" means or 4-methyl-2-pentanone and "THF" means tetrahydrofuran.

Example 1

A mixture of 1-[3-(4-fluorophenoxy)-propyl]-3-methoxy-4-piperidinone (140 mg, intermediate 1), benzylamine (61 mg), Pd 10% on charcoal (100 mg) and a 0.02% solution of thiophene in THF was reacted under hydrogen gas for 3 hours at 50° C. The catalyst was filtered off and fresh palladium 10% on charcoal (100 mg) was added. Debenzylation of the formed intermediate took place under hydrogen atmosphere for 18 hours at 50° C. The reaction mixture was filtered and evaporated under a gentle stream of nitrogen to yield 1-[3-(4-fluorophenoxy)-propyl]-3-methoxy-4-piperidinamine (compound I-1) having a cis/trans ratio of about 93/7.

Example 2 a) Compound (I-1) (50 g) was dissolved in methyl isobutylketone (250 ml) and a nitric acid solution (65%, 12.8 ml) was carefully added so that the temperature of the solution did not exceed 45° C. The reaction mixture was stirred at a temperature of 30° C. and seeded. When crystallisation started, the reaction mixture was cooled to 0° C. and stirred for another 2 hours. The product was filtered off, washed with a small amount of toluene and dried, yielding 1-[3-(4-fluorophenoxy)-propyl]-3-methoxy-4-piperidinamine.HNO$_3$ (mp. 60° C.).

b) 1-[3-(4-fluorophenoxy)-propyl]-3-methoxy-4-piperidinamine.HNO$_3$ was dissolved in water (95 ml). The reaction mixture was stirred and toluene (95 ml) was added. A NaOH solution (50%, 10.3 ml) was slowly added and the temperature of the reaction mixture was raised to 75° C. After 30 minutes, the aqueous layer was discarded and the organic layer was evaporated, yielding 1-[3-(4-fluorophenoxy)-propyl]-3-methoxy-4-piperidinamine (intermediate 2) having a cis/trans ratio equal to or higher than 98/2.

Example 3

To a solution of 4-amino-5-chloro-2-methoxybenzoic acid (20.2 g) in MIK (250 ml) and triethyl amine (15.3 ml) was slowly dropped ethyl chloroformate (9.6 ml). The reaction mixture was stirred for 30 minutes at room temperature. To the formed mixed anhydride was then added intermediate 2 (28.2 g) and the reaction mixture was stirred for 2 hours at room temperature. Subsequently, the reaction mixture was washed with water (80 ml) and a NaOH solution (6.5% w/v, 50 ml). The organic layer was warmed to 65° C. and methanol (50 ml) and water (8.5 ml) were added. The solution was cooled slowly and stirred for 2 days during which crystallisation occurred, yielding cisapride having a cis/trans ratio higher than 99/1.

What is claimed is:

1. A process of preparing a mixture of cis- and trans-1-[3-(4-fluorophenoxy)-propyl]-3-methoxy-4-piperidinamine (I-1) having a cis/trans ratio equal to or higher than 98.4/1.6 characterized in that

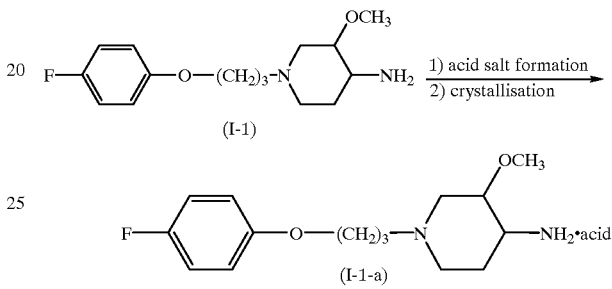

compound (I-1), having a cis/trans ratio less than 98.4/1/6, is converted to an acid addition salt by treating said compound (I-1) with an inorganic acid selected from nitric acid and hydrochloric acid, in an appropriate solvent selected from isopropanol, n-butanol, MIK and toluene, yielding after crystallization compound (I-1-a), having a cis/trans ratio equal to or higher than 98.4/1.6.

2. A process according to claim 1 wherein the inorganic acid is nitric acid.

3. A process according to claim 1 wherein the inorganic acid is hydrochloric acid.

4. A process according to claim 1 wherein the inorganic acid is nitric acid and the solvent is n-butanol.

5. A process according to claim 1 wherein the inorganic acid is nitric acid and the solvent is MIK.

6. A compound of formula (I-1-a) obtainable by the processes of the claim 1 and having a cis/trans ratio equal to or higher than 98.4/1.6

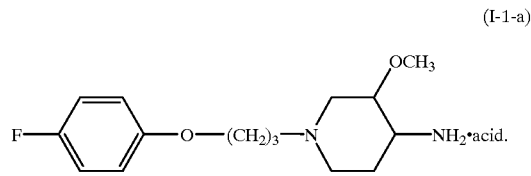

7. A compound according to claim 6 wherein the compound is 1-[3-(4-fluorophenoxy)propyl]-3-methoxy-4-piperidinamine nitrate.

8. A compound according to claim 6 wherein the compound is 1-[3-(4-fluorophenoxy)propyl]-3-methoxy-4-piperidinamine hydrochloride.

9. A process of preparing cisapride and the pharmaceutically acceptable acid addition salts thereof, comprising the steps of a) reductively aminating compound (1);

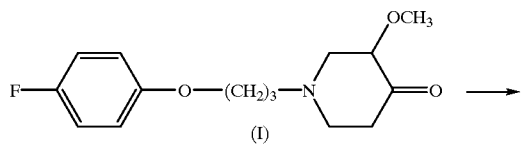

b) enriching the amount of cis-stereoisomer of compound (I-1) by converting compound (I-1) into an acid addition salt of formula (I-1-a), by treatment with an inorganic acid selected from nitric acid and hydrochloric acid, in an appropriate solvent selected from isopropanol, n-butanol, MIK and toluene, subsequent crystallization, and optional conversion to the free base form by treatment with an appropriate base, yielding compound (I-1) enriched in the amount of cis-stereoisomer;

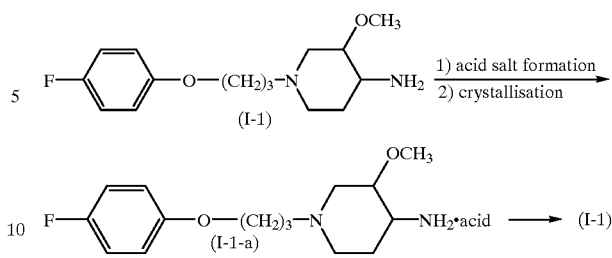

c) reacting the cis-stereoisomer enriched compound (I-1) or (I-1-a) with 4-amino-5-chloro-2-methoxybenzoic acid (3), or a functional derivative thereof, yielding cisapride (4)

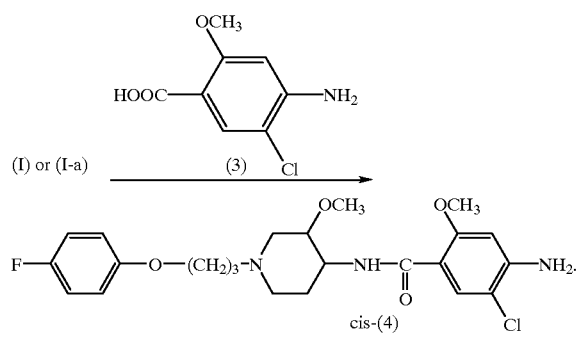

* * * * *

UNITED STATES PATENT AND TRADEMARK OFFICE
CERTIFICATE OF CORRECTION

PATENT NO. : 6,218,542 B1
DATED : April 17, 2001
INVENTOR(S) : Alfons Gaston Maria De Knaep, Luc Josef Raphael Moens, Max Rey It is certified that error appears in the above-identified patent and that said Letters Patent is hereby corrected as shown below:

<u>Title page,</u>
Item [73], please delete "Jenssen Pharmaceutica N.V." and insert -- Janssen Pharmaceutica, N.V. --

Signed and Sealed this

Twelfth Day of March, 2002

*Attest:*

JAMES E. ROGAN
*Director of the United States Patent and Trademark Office*

*Attesting Officer*